United States Patent [19]

Edwards

[11] 4,263,289

[45] Apr. 21, 1981

[54] THIO ETIANIC ACID DERIVATIVES

[75] Inventor: John A. Edwards, Los Altos, Calif.

[73] Assignee: Syntex (U.S.A.) Inc., Palo Alto, Calif.

[21] Appl. No.: 71,635

[22] Filed: Aug. 31, 1979

Related U.S. Application Data

[63] Continuation-in-part of Ser. No. 893,388, Jun. 5, 1978, Pat. No. 4,188,385.

[51] Int. Cl.³ .............................................. A61K 31/56
[52] U.S. Cl. .................................. 424/238; 260/397.1
[58] Field of Search ....................... 260/397.1; 424/238

[56] References Cited

U.S. PATENT DOCUMENTS 4,188,385  2/1980  Edwards .................... 260/239.55 D

*Primary Examiner*—Elbert L. Roberts
*Attorney, Agent, or Firm*—Tom M. Moran; Alan M. Krubiner

[57] ABSTRACT

Certain 16β-methyl-3-oxoandrost-4-ene and 16β-methyl-3-oxoandrosta-1,4-diene 17β-thiocarboxylic acid esters are useful as anti-inflammatory steroids. These compounds are optionally substituted at the 6α-position with fluoro or chloro; optionally substituted at the 9α position with fluoro, chloro or bromo; substituted at the 11 position with a keto, a β-hydroxy or a β-chloro (the latter only when there is a 9α-chloro); and substituted with 17α-hydroxy (or an ester thereof).

7 Claims, No Drawings

THIO ETIANIC ACID DERIVATIVES

This is a continuation-in-part of U.S. patent application Ser. No. 893,388 filed June 5, 1978, now U.S. Pat. No. 4,188,385, issued Feb. 12, 1980.

BACKGROUND OF THE INVENTION

1. Field of the Invention

This invention relates to novel derivatives of alkyl, phenyl or benzyl 16β-methyl-3-oxoandrost-4-ene-17β-thiocarboxylates and the corresponding androsta-1,4-dienes which are active anti-inflammatory agents in mammals. The invention further relates to pharmaceutically active compositions comprising a selected 17β-thiocarboxylate of the invention in combination with a pharmaceutically acceptable excipient.

2. Prior Art

Certain 3-oxoandrost-4-ene 17β-carboxylic acids which are substituted at the 9 position with chlorine or fluorine and at the 11 position with keto or hydroxy or chloro group are known. See for example U.S. Pat. Nos. 3,828,080 and 3,981,894 both to Phillipps et al. It is also known that 3-oxoandrost-4-ene 17β-carboxylic acids or esters thereof may be substituted at the 6α position with fluoro and optionally at the 9α position with a fluoro. See for example U.S. Pat. No. 3,636,010 and U.S. Pat. No. 4,093,721 to Phillipps.

It is also known from U.S. Pat. No. 3,989,686 to Phillipps et al of Glaxo that steroids of the formula

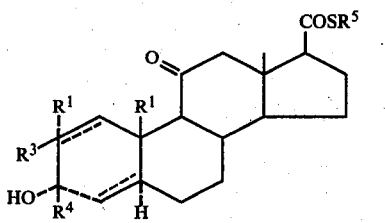

wherein
$R^1$ is H or $CH_3$;
$R^2$ is H or $CH_3$;
$R^3$ is H or, when $R^2$ is H, $C_{1-6}$ alkoxy, $C_{1-5}$ alkyl, thiocyanato or halogen;
$R^4$ is H or $CH_3$;
$R^5$ is $C_{1-6}$ alkyl optionally substituted by halo or $NR^6R^7$, where $R^6$ and $R^7$ are the same or different $C_{1-6}$ alkyl or $R^6$ and $R^7$ together with N are morpholino, thiamorpholine or morpholino substituted with $C_{1-6}$ alkyl; and
the dotted line in the "A" ring represents an optional double bond at these positions. These compounds are useful as anesthetics.

Methyl 3β-acetoxyallothiolcholonate and methyl 3β-acetoxy-etiothiochol-5-enate are also known. See, e.g., Jerger et al, Helv. Chem. Acta. 29, 684–92 (1947).

A heretofore unknown series of 16β-methyl-3-oxoandrost-4-ene 17β-thiocarboxylates and derivatives thereof has been discovered and is disclosed herein. The 17β-thiocarboxylates exhibit topical anti-inflammatory activity and few adverse side effects.

SUMMARY OF THE INVENTION

One aspect of this invention is a compound chosen from those represented by the formula

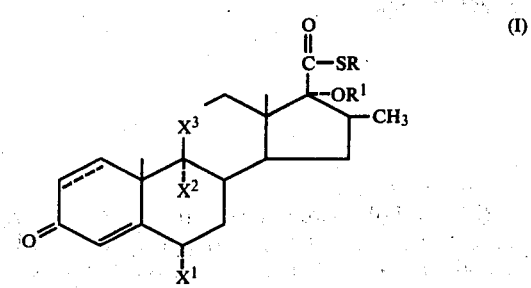

wherein
$X^1$ is hydrogen, fluoro, or chloro;
$X^2$ is hydrogen, fluoro, chloro or bromo;
$X^3$ is

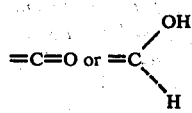

or may also be

when $X^2$ is chloro;
R is alkyl of 1 through 6 carbon atoms, or phenyl or benzyl optionally subtituted with a substituent which is alkyl of 1 through 4 carbon atoms, alkoxy of 1 through 4 carbon atoms or halo;
$R^1$ is hydrogen or alkanoyl of 2 through 6 carbon atoms; and
the bond between C-1 and C-2 is a double or single bond.

Another aspect of this invention is a topical anti-inflammatory pharmaceutical composition which comprises a suitable pharmaceutical excipient in combination with an effective amount of a suitable compound chosen from those represented by Formula (I), above, wherein each of the substituents are as defined. Particularly valuable compounds in this composition are set forth hereafter.

Still another aspect of this invention is a method for treating an inflamed condition in mammals which comprises treating the afflicted mammal with an effective amount of a suitable compound chosen from those represented by formula (I), above, wherein substituents are as defined above.

DETAILED DESCRIPTION

Compounds

In its broadest aspect, this invention is a compound chosen from those represented by Formula (I) wherein
$X^1$ is hydrogen, fluoro, or chloro;
$X^2$ is hydrogen, fluoro, chloro or bromo;
$X^3$ is

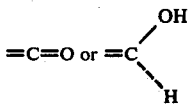

or may also be

when X² is chloro;

R is alkyl of 1 through 6 carbon atoms, or phenyl or benzyl optionally substituted with a substituent which is alkyl of 1 through 4 carbon atoms, alkoxy of 1 through 4 carbon atoms or halo;

R¹ is hydrogen or alkanoyl of 2 through 6 carbon atoms; and the bond between C-1 and C-2 is a double or single bond.

One subgroup of the broad aspect of this invention includes the compounds represented by Formula (I) wherein R is alkyl of 1–6 carbon atoms, phenyl or benzyl; X¹ is fluoro or hydrogen; X² is fluoro, chloro or hydrogen; and X³ is

or may also be

when X² is chloro. Of this subgroup the compound wherein R is methyl or ethyl, X² is hydrogen or fluoro and X³ is

are preferred. Particularly preferred are those compounds wherein X¹ and X² are both fluoro. In each group or subgroup the compounds preferred are those with a double bond between C-1 and C-2.

Representative examples of the compounds of this invention are set forth hereafter in the Examples.

In defining the compounds of this invention the term "alkyl" includes both straight chain and branched alkyl groups, thus "alkyl" of 1-6 carbons includes methyl, ethyl, n-propyl, isopropyl, n-butyl, isobutyl, t-butyl, pentyl, isoamyl, n-hexyl and the like. The phenyl and benzyl substituents may be substituted on the phenyl ring at the 2, 3 or 4-positions with one substituent such as alkoxy (e.g. methoxy, ethoxy, n-propoxy, t-butoxy and the like), alkyl of 1-4 carbons (e.g. methyl, ethyl, isopropyl, n-propyl, t-butyl, n-butyl, etc.), or a halo such as fluoro, chloro, bromo or iodo. Preferably the substitution is at the 2 or 4 positions.

The term "alkanoyl" refers to a radical of the formula

wherein R⁴ is alkyl of 1–5 carbon atoms and includes, e.g., acetyl, propionyl, butyryl, valeryl, caproyl and the like.

In naming the compounds of this invention the substituents present on the androstane ring shall be included alphabetically and the compounds shall be alkyl (or phenyl or benzyl) 17β-carboxylates. For example, if in formula (I), above, X¹ is fluoro, X² is chloro, X³ is

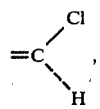

R is methyl and R¹ is acetoxy, the name is methyl 17α-acetoxy-9α,11β-dichloro-6α-fluoro-16β-methyl-3-oxo-androsta-1,4-diene-17β-thiocarcarboxylate. If on the other hand, R is hydrogen but X¹, X², X³, X⁴ and R¹ are the same, the compound is named 17α-acetoxy-9α,11β-dichloro-6α-fluoro-16β-methyl-3-oxoandrosta-1,4-diene 17β-thiocarboxylic acid.

Compound Preparation

The compounds of the invention are prepared by reacting an appropriate androsta-1,4-diene 17β-carboxylic acid (or the corresponding 4-ene) or a reactive derivative, with an excess (e.g. about 1.1 to 5 molar equivalents based on the steroid) of alkali metal salt of a compound of the formula RSH where R is alkyl, benzyl or phenyl as defined hereinbefore. Representative alkali metal salts include, e.g., sodium methyl mercaptan, sodium ethyl mercaptan, sodium benzyl mercaptan, sodium phenyl mercaptan, potassium methyl mercaptan, and the like. The alkali metal salt can be reacted directly with the reactive derivative of the 17β-carboxylic acid, or the salt can be formed in situ by mixing an alkali metal hydride, such as sodium hydride or potassium hydride, with an alkyl, phenyl or benzyl mercaptan. The thioesterification reaction readily takes place at temperatures of about 10° to 100° C. (preferably at ambient temperatures of about 20°–25° C.) in a suitable inert solvent such as dimethylformamide, diethylformamide, dimethylacetamide, and the like. The reactive derivative of the 17β-carboxylic acid may be an acid chloride, but is preferably a mixed anhydride, such as the dialkyl or diphenyl phosphate ester prepared by reacting a dialkyl (1-4 carbons) chlorophosphate (e.g. diethyl chlorophosphate) or diphenyl chlorophosphate with the appropriate 17β-carboxylic acid in an inert solvent such as tetrahydrofuran (THF) under an inert atmosphere (nitrogen).

The 17β-carboxylic acid starting materials are prepared by eliminating the 21 carbon atom from a suitable 21-hydroxy-3,20-dioxopregn-4-ene or pregna-1,4-diene. This is readily accomplished by any means known in the art such as using sodium hypobromite as taught in U.S. Pat. No. 2,769,822 or using periodic acid in aqueous methanol at room temperature to oxidize an appropriate 21-hydroxy pregnanes.

Suitable 21-hydroxy-3,20-dioxopregn-4-enes or -pregna-1,4-dienes include known compounds such as 16β-methyl prednisolone, betamethasone, 6α-fluoro-betamethasone, 6α-fluoro-16β-methylprednisolone, and the like. By following procedures generally known in the art steroids of a relatively simple structure can be converted to other structures as desired.

For example, the 6-fluoro starting steroids can be prepared from known steroids such as 17α-hydroxyprogesterone or hydrocortisone. The 6-fluoro group can be introduced by treating a 3-methoxy-pregna-3,5-diene (prepared by reacting a 3-keto-pregn-4-ene with triethyl orthoformate in methanol) with perchloryl fluoride in acetone-water 9:1.

Other 6-fluoro starting steroids employed in the present process to prepare the novel 17β-thiocarboxylic acid derivatives of this invention are described in the literature and in United States and foreign patents. For example, see U.S. Pat. No. 2,983,737, 2,983,739, 3,053,838, 3,057,858, 3,124,251, 3,126,375, 3,201,391 and 3,248,389.

The 9α-fluoro, chloro or bromo group is introduced by treating a 9β,11β-oxido steroid with hydrogen fluoride, hydrogen chloride or hydrogen bromide respectively in an inert, nonaqueous, preferably anhydrous, solvent or mixture of such solvents. For example, see U.S. Pat. No. 3,211,758 to Tarkoey wherein a hydrogen fluoride/urea complex is employed. The 9β,11β-oxido steroid is prepared from the corresponding pregna-4,9(11)-diene (which is prepared by treating the corresponding 11β-hydroxy steroid with methane sulfonyl chloride in dimethylformamide in the presence of pyridine and a catalytic amount of sulfur trioxide) by treating the pregna-4,9(11)-diene with N-bromoacetamide and perchloric acid in dioxane or tetrahydrofuran, and then refluxing the resulting 9-bromo-11-hydroxy steroid with potassium acetate in acetone. The 9α,11β-dichloro groups are introduced by treating the corresponding pregna-4,9(11)-diene with chlorine gas in chloroform.

The 17α-hydroxy group is introduced in conjunction with the 16β-methyl group by first treating the corresponding 16-methyl-pregn-16-ene (which is prepared by treating the corresponding pregn-16-ene with diazomethane and then heating the resulting product to 180° C.) with hydrogen peroxide, in an aqueous basic media, then permitting the resulting 16,17-oxido-16-methyl steroid to react with hydrogen bromide in glacial acetic acid. The resulting 16,17-bromohydrin is hydrogenated with the use of a palladium catalyst to afford the corresponding 16β-methyl-17α-hydroxy derivative.

Administration and Formulation

The compounds of this invention are useful for the relief of inflamed conditions in mammals, and more specifically are useful for relieving inflammatory manifestations of corticosteroid responsive dermatoses. Initial approximation of anti-inflammatory activity is done by the following procedure of McKenzie, S. W. and Stoughton, R. B., "Method for Comparing Percutaneous Absorption of Steroids" Arch Dermat, 86, 608 (1962) or modifications thereof.

Generally, this inflammatory manifestation in mammals, particularly humans, is combatted by treating the afflicted mammal with a therapeutically effective amount of the novel steroids of this invention, that is an amount which results in improvement of the inflamed conditions.

Preferably the steroids are first formulated to prepare a suitable pharmaceutical formulation, as discussed hereinafter, which is then placed in contact with the afflicted area. An effective amount will depend upon the particular condition and the animal receiving the treatment but will vary between 0.001% to 10% by weight of the pharmaceutical composition and preferably will be between 0.02 and 1% by weight of the formulation. Using these levels in the formulation, a therapeutically effective and non-side effect producing amount, i.e. enough to effect an anti-inflammatory response, but not enough to adversely effect the recipient, is applied to the inflamed area.

The compounds of this invention not only have anti-inflammatory activity but also exhibit a low level of systemic activity, as measured by recognized laboratory assays. This allows for the application of an effective amount of the anti-inflammatory compounds with little adverse effect on the rest of the animal's system.

The novel steroids of this invention may be formulated with suitable pharmaceutical excipients known in the art to form particularly effective anti-inflammatory compositions which may be administered orally, nasally, rectally or, preferably, topically. Generally an effective amount of the steroid is about 0.001%w to about 10%w of the total formulated composition. The rest of the formulated composition will be about 90%w to about 99.999%w of suitable excipients which may include a pharmaceutically acceptable solvent and other pharmaceutically acceptable additives to form an effective pharmaceutical formulation. The composition is prepared by dissolving the active ingredient in the desired solvent and mixing with the other excipients as required.

A pharmaceutically acceptable solvent is one which is substantially non-toxic and no-irritating under the conditions used and may be readily formulated into any of the classical drug formulations such as powders, creams, ointments, lotions, gels, foams, suppositories, aerosols, solutions or the like. Particularly suitable solvents include water, glycerine, propylene carbonate, and a glycol such as 1,2-propylene diol (i.e. propylene glycol), 1,3-propylene diol, polyethylene glycol having a molecular weight of from 100 to 10,000, dipropylene glycol, etc.; and mixtures of the aforementioned with each other.

A topical cream may be prepared as a semi-solid emulsion of oil in water or water in oil. A cream base formulation by definition is an emulsion which is a two-phase system with one liquid (for example fats or oils) being dispersed as small globules in another substance (e.g., a glycol-water solvent phase) which may be employed as the primary solvent for the novel steroids therein, the cream formulation may contain fatty alcohols, surfactants, mineral oil or petrolatum and other typical pharmaceutical adjuvants such as antioxidants, antiseptics, or compatible adjuvants. A typical cream base formulation is given in the following table:

| | |
|---|---|
| Water/glycol mixture (15% or more glycol) | 50–99 parts by weight |
| Fatty alcohol | 1–20 |
| Non-ionic Surfactant | 0–10 |
| Mineral oil | 0–10 |
| Typical pharmaceutical adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The novel steroids of this invention may also be formulated as ointments. A "classical" ointment is a semi-solid anhydrous composition which may contain mineral oil, white petrolatum, a suitable solvent such as a glycol and may include isopropylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| White petrolatum | 40–94 | parts by weight |
|---|---|---|
| Mineral Oil | 5–20 | |
| Glycol solvent | 1–15 | |
| Surfactant | 0–10 | |
| Stabilizer | 0–10 | |
| Active Ingredients | 0.001–10.0 | |

Other suitable ointment base formulations which employ propylene carbonate are described in U.S. Pat. No. 4,017,613 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| Active Ingredients | 0.001–10.0 | parts by weight |
|---|---|---|
| Propylene Carbonate | 1–10 | |
| Solvent | 1–10 | |
| Surfactant | 1–10 | |
| White Petrolatum | 70–97 | |

Surfactants, stabilizers, etc. are discussed in U.S. Pat. No. 3,934,013 and such discussion is incorporated herein by reference.

A suitable "non-classical" anhydrous, water washable "ointment type" base is described in U.S. Pat. No. 3,952,930 to Katz and Neiman, and that patent is incorporated herein by reference. A representative composition of this invention utilizing such a base is as follows:

| Glycol solvent | 50–35 | parts by weight |
|---|---|---|
| Fatty alcohol | 15–45 | |
| Compatible plasticizer | 0–15 | |
| Compatible coupling Agent | 0–15 | |
| Penetrant | 0–20 | |
| Active Ingredients | 0.001–10.0 | |

Preparation 1

A process is set forth for preparing 17α-hydroxy-16β-methyl-3-oxoandrosta-1,4-diene 17β-carboxylic acids substituted at the 9α-position with hydrogen, fluoro, chloro or bromo; at the 6α-position with hydrogen, fluoro or chloro; and at the 11β-position with hydroxy or chloro when 9α is chloro substituted.

A. 9α-Fluoro-11β, 17α-dihydroxy-16β-methyl-3-oxoandrosta-1,4-diene 17β-carboxylic acid Thirty-five grams of betamethasone is mixed with 550 ml of methanol and 35 g of anhydrous potassium carbonate and stirred at room temperature and atmospheric pressure while a current of air is slowly bubbled through the solution for 22 hours. Methanol is added at intervals to maintain a constant volume. The reaction mixture is diluted with water to 1.5 l, then concentrated hydrochloric acid is added slowly to the mixture under magnetic stirring until a final pH of 2 is obtained. Methanol is eliminated under reduced pressure, and the resulting crystalline precipitate is collected by filtration, washed with water, and air dried to give 9α-fluoro-11β,17α-dihydroxy-16β-methyl-3-oxoandrosta-1,4-diene 17β-carboxylic acid, melting point (m.p.).

B. By following the procedure set forth in part A of this example but substituting other appropriate starting materials for betamethasone the following compounds of this invention can be prepared:

11β,17α-hydroxy-16β-methyl-3-oxoandrosta-1,4-diene 17β-carboxylic acid;

6α-fluoro-11β,17α-dihydroxy-16β-methyl-3-oxoandrosta-1,4-diene 17β-carboxylic acid;

6α,9α-difluoro-11β,17α-dihydroxy-16β-methyl-3-oxoandrosta-1,4-diene 17β-carboxylic acid;

9α,11β-dichloro-6α-fluoro-17α-hydroxy-16β-methyl-3-oxoandrosta-1,4-diene 17β-carboxylic acid;

9α-chloro-6α-fluoro-11β,17α-dihydroxy-16β-methyl-3-oxo-androsta-1,4-diene 17β-carboxylic acid;

9α-bromo-6α-fluoro-11β,17α-dihydroxy-16β-methyl-3-oxo-androsta-1,4-diene 17β-carboxylic acid;

9α,11β-dichloro-17α-dihydroxy-16β-methyl-3-oxo-androsta-1,4-diene 17β-carboxylic acid;

9α-chloro-11β,17α-dihydroxy-16β-methyl-3-oxo-androsta-1,4-diene 17β-carboxylic acid;

9α-bromo-11β,17α-dihydroxy-16β-methyl-3-oxo-androsta-1,4-diene 17β-carboxylic acid;

6α,9α-dichloro-11β,17α-dihydroxy-16β-methyl-3-oxo-androsta-1,4-diene 17β-carboxylic acid;

6α-chloro-9α-fluoro-11β,17α-dihydroxy-16β-methyl-3-oxo-androsta-1,4-diene 17β-carboxylic acid;

9α-bromo-6α-chloro-11β,17α-dihydroxy-16β-methyl-3-oxo-androsta-1,4-diene 17β-carboxylic acid;

6α-chloro-11β,17α-dihydroxy-16β-methyl-3-oxo-androsta-1,4-diene 17β-carboxylic acid; and 6α,9α-dichloro-11β,17α-dihydroxy-16β-methyl-3-oxo-androsta-1,4-diene 17β-carboxylic acid.

Preparation 2

A. Ten g of a compound prepared according to Part A of Preparation 1 is dissolved in 100 ml methanol. Fifty ml of anhydrous pyridine and 25 ml of propionic anhydride are added and the resulting mixture stirred until TLC shows the reaction is complete. The solution is cooled in an ice-water bath and slowly diluted with water up to two l. The resulting crystalline precipitate is collected by filtration and air dried to give the 9α-fluoro-11β-hydroxy-16β-methyl-3-oxo-17α-propionyloxyandrosta-1,4-diene 17β-carboxylic acid.

B. By following in principle the process of Part A of this preparation, but substituting other 17β-carboxylic acids prepared according to Part B of Preparation 1 for 9α-fluoro-11β,17α-dihydroxy-16β-methyl-3-oxoandrosta-1,4-diene 17β-carboxylic acid, other compounds are prepared such as 11β-hydroxy-16β-methyl-3-oxo-17α-propionyloxyandrosta-1,4-diene 17β-carboxylic acid;

6α-fluoro-11β-hydroxy-16β-methyl-3-oxo-17α-propionyloxyandrosta-1,4-diene 17β-carboxylic acid;

6α,9α-difluoro-11β-hydroxy-16β-methyl-3-oxo-17α-propionyloxyandrosta-1,4-diene 17β-carboxylic acid;

9α,11β-dichloro-6α-fluoro-16β-methyl-3-oxo-17α-propionyloxyandrosta-1,4-diene 17β-carboxylic acid; and other 17α-propionates corresponding to the compounds delineated Part A of Preparation 1.

C. By following in principle the process of Parts A and B of this preparation, but substituting other anhydrides such as acetic anhydride, butyric anhydride, caproic anhydride, etc. for propionic anhydride other compounds are prepared such as 17α-acetoxy-9α-fluoro-11β-hydroxy-16β-methyl-3-oxoandrosta-1,4-diene 17β-carboxylic acid;

17α-acetoxy-11β-hydroxy-16β-methyl-3-oxoandrosta-1,4-diene 17β-carboxylic acid;

17α-acetoxy-6α-fluoro-11β-hydroxy-16β-methyl-3-oxoandrosta-1,4-diene 17β-carboxylic acid;

17α-acetoxy-6α,9α-difluoro-11β-hydroxy-16β-methyl-3-oxoandrosta-1,4-diene 17β-carboxylic acid;

17α-butyroxy-9α-fluoro-16β-methyl-3-oxoandrosta-1,4-diene 17β-carboxylic acid;

17α-butyroxy-11β-hydroxy-16β-methyl-3-oxoandrosta-1,4-diene 17β-carboxylic acid;

17α-butyroxy-6α-fluoro-11β-hydroxy-16β-methyl-3-oxoandrosta-1,4-diene 17β-carboxylic acid;

17α-butyroxy-6α,9α-difluoro-11β-hydroxy-16β-methyl-3-oxoandrosta-1,4-diene 17β-carboxylic acid;

17α-butyroxy-9α,11β-dichloro-11β-hydroxy-16β-methyl-3-oxoandrosta-1,4-diene 17β-carboxylic acid;

17α-capropyloxy-9α-fluoro-11β-hydroxy-16β-methyl-3-oxoandrosta-1,4-diene 17β-carboxylic acid;

17α-caproyloxy-6α-fluoro-16β-methyl-3-oxoandrosta-1,4-diene 17β-carboxylic acid;

17α-capropyloxy-6α,9α-difluoro-16β-methyl-3-oxoandrosta-1,4-diene 17β-carboxylic acid;

17α-caproyloxy-9α,11β-dichloro-16β-methyl-3-oxoandrosta-1,4-diene 17β-carboxylic acid; and the like.

Specific embodiments of the process of this invention are found in the following Examples which are given by way of illustration only and are not to be interpreted as limiting the scope of the claims appended hereto.

EXAMPLE 1

A process is set forth for preparing alkyl, benzyl or phenyl 17α-alkanoyloxy-16β-methyl-3-oxoandrosta-1,4-diene 17β-thiocarboxylates of this invention which are substituted with hydrogen, fluoro or chloro at the 6α-position; with fluoro, chloro, bromo or hydrogen at the 9α-position; and 11β-hydroxy or 11β-chloro when there is a chloro at 9α.

A. Methyl 9α-fluoro-11β-hydroxy-16β-methyl-3-oxo-17-propionyloxyandrosta-1,4-diene 17β-thiocarboxylate.

9α-Fluoro-11β-hydroxy-16β-methyl-3-oxo-17-propionyloxyandrosta-1,4-diene 17β-carboxylic acid, prepared in the manner set forth in Preparation 1, Part A, is mixed with THF and triethylamine (TEA) in a suitable reaction vessel and stirred at room temperature under $N_2$. Thereafter, diethyl chlorophosphate (DCP: $C_2H_5O)_2P(O)Cl$) in THF is added over about 15 minutes. Stirring is continued at pH 6 for about 4 hours and TEA is added followed by DCP in THF. Stirring is continued until a substantial amount of precipitate is formed which is then filtered, washed with THF and the filtrates are combined. To the filtrate is then added a solution prepared previously which consists of dimethylformamide (DMF), 75% sodium hydride and (1 ml) methylmercaptan. The resulting reaction mixture of the filtrates and the DMF solution is stirred for several hours and an additional amount of the DMF solution is added and stirring is continued until t.l.c. indicates the reaction is complete.

The reaction mixture is then poured into ethyl acetate (EtOAc) which, in turn, is washed twice with portions of water, washed with brine, dried over sodium sulfate and filtered. The solvents are then removed under reduced pressure using a rotary evaporator to give a residue which is recrystallized from acetone/hexane to give methyl 9α-fluoro-11β-hydroxy-16β-methyl-17α-propionyloxyandrosta-1,4-diene 17β-thiocarboxylate.

B. By following in principle the procedure of Part A of this example but substituting other mercaptans such as ethyl mercaptan, isopropyl mercaptan, n-butyl mercaptan, hexyl mercaptan, phenyl mercaptan, or benzyl mercaptan for methyl mercaptan other compounds of this invention are prepared, namely ethyl 9α-fluoro-11β-hydroxy-16β-methyl-3-oxo-17α-propionyloxyandrosta-1,4-diene 17β-thiocarboxylate;

isopropyl 9α-fluoro-11β-hydroxy-16β-methyl-3-oxo-17α-propionyloxyandrosta-1,4-diene 17β-thiocarboxylate;

n-butyl 9α-fluoro-11β-hydroxy-16β-methyl-3-oxo-17α-propionyloxyandrosta-1,4-diene 17β-thiocarboxylate;

hexyl 9α-fluoro-11β-hydroxy-16β-methyl-3-oxo-17α-propionyloxyandrosta-1,4-diene 17β-thiocarboxylate;

phenyl 9α-fluoro-11β-hydroxy-16β-methyl-3-oxo-17α-propionyloxyandrosta-1,4-diene 17β-thiocarboxylate;

benzyl 9α-fluoro-11β-hydroxy-16β-methyl-3-oxo-17α-propionyloxyandrosta-1,4-diene 17β-thiocarboxylate;

C. By following in principle the process of Part A of this example, but substituting other appropriate steroids for 9α-fluoro-11β-hydroxy-16α-methyl-3-oxo-17-propionyloxyandrosta-1,4-diene 17β-carboxylic acid, other compounds of this invention are obtained such as methyl 11β-hydroxy-16β-methyl-3-oxo-17α-propionyloxyandrosta-1,4-diene 17β-thiocarboxylate;

methyl 6α-fluoro-11β-hydroxy-16β-methyl-3-oxo-17α-propionyloxyandrosta-1,4-diene 17β-thiocarboxylate;

methyl 6α,9α-difluoro-11β-hydroxy-16β-methyl-3-oxo-17α-propionyloxyandrosta-1,4-diene 17β-thiocarboxylate; and methyl 9α,11β-dichloro-6α-fluoro-16β-methyl-3-oxo-17α-propionyloxyandrosta-1,4-diene 17β-thiocarboxylate;

methyl 17α-acetoxy-9α-fluoro-11β-hydroxy-16β-methyl-3-oxoandrosta-1,4-diene 17β-thiocarboxylate;

methyl 17α-acetoxy-11β-hydroxy-16β-methyl-3-oxoandrosta-1,4-diene 17β-thiocarboxylate;

methyl 17α-acetoxy-6α-fluoro-11β-hydroxy-16β-methyl-3-oxoandrosta-1,4-diene 17β-thiocarboxylate;

methyl 17α-acetoxy-6α,9α-difluoro-11β-hydroxy-16β-methyl-3-oxoandrosta-1,4-diene 17β-thiocarboxylate;

methyl 17α-butyroxy-9α-fluoro-16β-methyl-3-oxoandrosta-1,4-diene 17β-thiocarboxylate;

methyl 17α-butyroxy-11β-hydroxy-16β-methyl-3-oxoandrosta-1,4-diene 17β-thiocarboxylate;

methyl 17α-butyroxy-6α-fluoro-11β-hydroxy-16β-methyl-3-oxoandrosta-1,4-diene 17β-thiocarboxylate;

methyl 17α-butyroxy-6α,9α-difluoro-11β-hydroxy-16β-methyl-3-oxoandrosta-1,4-diene 17β-thiocarboxylate;

methyl 17α-butyroxy-9α,11β-dichloro-11β-hydroxy-16β-methyl-3-oxoandrosta-1,4-diene 17β-thiocarboxylate;

methyl 17α-caproyloxy-9α-fluoro-11β-hydroxy-16β-methyl-3-oxoandrosta-1,4-diene 17β-thiocarboxylate;

methyl 17α-caproyloxy-6α-fluoro-16β-methyl-3-oxoandrosta-1,4-diene 17β-thiocarboxylate;

methyl 17α-caproyloxy-6α,9α-difluoro-16β-methyl-3-oxoandrosta-1,4-diene 17β-thiocarboxylate;

methyl 17α-capropyloxy-9α,11β-dichloro-16β-methyl-3-oxoandrosta-1,4-diene 17β-thiocarboxylate; and the like.

EXAMPLE 2

A process is set forth for preparing alkyl, benzyl or phenyl 17α-hydroxy-16β-methyl-3-oxoandrosta-1,4-diene 17β-thiocarboxylates of this invention which are substituted at the 6α-position with fluoro, chloro or hydrogen; at the 9α-position with hydrogen, fluoro, chloro or bromo; and at the 11β-position with hydroxy or also chloro when there is a 9α-chloro.

A. Ethyl 9α-fluoro-11β,17α-dihydroxy-16β-methyl-3-oxoandrosta-1,4-diene 17β-thiocarboxylate.

9α-Fluoro-11β,17α-dihydroxy-16β-methyl-3-oxoandrosta-1,4-diene 17β-carboxylic acid is dissolved in DMF and cooled to −10° C. Carbonyl diimidazole (CDI) is dissolved in DMF, and this solution is added to the DMF/acid solution under a nitrogen blanket. The resulting mixture is stirred at −5° C. and ethyl sulfide (EtSH) is added thereto. The reaction is stirred at −5° C. until t.l.c. indicates that thereaction is complete.

The solvents are removed under reduced pressure from reaction mixture and the residue is applied to a 1 meter X 0.75 TLC plate and developed twice with a mixtuure of 10% acetone/90% benzene. After recovery, the material is recrystallized from acetone/hexane to give ethyl 9α-fluoro-11β,17α-dihydroxy-16β-methyl-3-oxoandrosta-1,4-diene 17β-thiocarboxylate.

B. Similarly, by following in principle the process of Part A of this example but substituting other alkyl, phenyl or benzyl mercaptans for ethyl mercaptan, other compounds of this invention such as methyl 9α-fluoro-11β,17α-dihydroxy-16β-methyl-3-oxoandrosta-1,4-diene 17β-thiocarboxylate;

isopropyl 9α-fluoro-11β,17α-dihydroxy-16β-methyl-3-oxoandrosta-1,4-diene 17β-thiocarboxylate;

n-butyl 9α-fluoro-11β,17α-dihydroxy-16β-methyl-3-oxoandrosta-1,4-diene 17β-thiocarboxylate;

n-hexyl 9α-fluoro-11β, 17α-dihydroxy-16β-methyl-3-oxoandrosta-1,4-diene 17β-thiocarboxylate;

phenyl 9α-fluoro-11β,17α-dihydroxy-16β-methyl-3-oxoandrosta-1,4-diene 17β-thiocarboxylate;

benzyl 9α-fluoro-11β,17α1 -dihydroxy-16β-methyl-3-oxoandrosta-1,4-diene 17β-thiocarboxylate; and the like.

C. Similarly, by following in principle the process of Part A or Part B but substituting other appropriate 17β-carboxylic acids prepared in the manner set forth in Preparation 1 for 9α-fluoro-11β,17α-dihydroxy-16α-methyl-3-oxoandrosta-1,4-diene 17β-carboxylic acid, other compounds of this invention are obtained such as the methyl, ethyl, propyl, isopropyl, butyl, isobutyl, n-hexyl, phenyl and benzyl derivatives of 11β,17α-dihydroxy-16β-methyl-3-oxoandrosta-1,4-diene 17β-thiocarboxylate;

6α-fluoro-11β,17α-dihydroxy-16β-methyl-3-oxoandrosta-1,4-diene 17β-thiocarboxylate;

6α,9α-difluoro-11β,17α-dihydroxy-16β-methyl-3-oxoandrosta-1,4-diene 17β-thiocarboxylate;

9α,11β-dichloro-6α-fluoro-17α-hydroxy-16β-methyl-3-oxoandrosta-1,4-diene 17β-thiocarboxylate; and the like.

EXAMPLE 3

This example sets forth a process for preparing an 11-keto compound of this invention by oxidizing any of the 11β-hydroxy steroids set forth in Preparations 1–2 and converting the so-obtained compound to the 17β-thiocarboxylate according to the process of Examples 1 and 2.

one g of 9α-fluoro-11β,17α-dihydroxy-16β-methyl-3-oxoandrosta-1,4-diene-17β-carboxylic acid is dissolved in 50 ml of acetone and treated at room temperature with Jones reagent (chromic anhydride in dilute sulfuric acid) dropwise until TLC indicates the absence of starting material. The mixture is treated with five drops of isopropyl alcohol to destroy any excess of reagent, then diluted with 50 ml of water and the mixture concentrated under vacuum under reduced pressure to give a crystalline material, namely 9α-fluoro-17α-hydroxy-16β-methyl-3,11-dioxoandrosta-1,4-diene-17β-carboxylic acid. This compound, in turn, is reacted according to the process of Example 2 to give methyl 9α-fluoro-17α-hydroxy-11-keto-16β-methyl-3-oxoandrosta-1,4-diene 17β-thiocarboxylate.

EXAMPLE 4

This example sets forth a process for converting an androsta-1,4-diene of this invention to the corresponding androst-4-ene.

To a solution of 25 mg of tris-(triphenylphosphine)-chlororhodium in 7 ml of benzene and 15 ml of ethanol, 244 mg methyl 9α-fluoro-11β,17α-dihydroxy-16β-methyl-3-oxoandrosta-1,4-diene 17-thiocarboxylate are added and the resulting solution is stirred under hydrogen at room temperature at atmospheric pressure. After hydrogen uptake is complete the solution is evaporated to dryness and the residue is taken up in a mixture of petroleum ether and methylene chloride. The pure product is isolated by column chromatography on silica gel to give methyl 9α-fluoro-11β,17α-dihydroxy-16β-methyl-3-oxoandrosta-4-ene 17β-thiocarboxylate. Similarly, by substituting other androsta-1,4-dienes of this invention made according to examples 1–3 for the compound used above in this example, other corresponding androsta-4-enes of the invention are prepared such as methyl 6α-fluoro-11β-hydroxy-16β-methyl 17α-propionyloxyandrost-1-ene 17β-thiocarboxylate, m.p. 210°–212° C.

EXAMPLE 5

In a heat-dried, stirred, N₂ blanketed 25 ml flask with side-arm septum 130 mg of 9α-fluoro-11β-hydroxy-16β-methyl-17α-propionyloxy-3-oxoandrosta-1,4-diene 17β-carboxylic acid is dissolved in 8 ml of dry THF. Fifty-nine (59) μl of triethylamine followed by 81 μl of diphenyl chlorophosphate are added, and the turbid mixture is heated in a 55° oil bath. After 2 hours the reaction is cooled in ice and then filtered into a fresh, dry N₂ blanketed 50 ml flask with side-arm and septum, washing filter cake with additional THF.

1.35 Ml of a 0.92 N solution of sodium thiomethylate (NaSCH₃) is added to the solution of the intermediate in the flask and the mixture is heated at 55° for 1½ hours, after which the reaction is complete. The resulting product is dumped into ethyl acetate and dilute aqueous sodium bicarbonate is added. The extract is washed three times with H₂O, dried over Na₂SO₄, and evaporated to dryness. Two crystallizations of the residue from acetone-hexane affords 67 mg of 98% pure colorless needles of the methyl 9α-fluoro-11β-hydroxy-16β-methyl-17α-propionyloxy-3-oxoandrosta-1,4-diene 17β-thiocarboxylate, m.p. 223°–224°.

EXAMPLE 6

In this example a formulation is prepared of the following composition

|  | % w/w |
|---|---|
| Methyl 9α-fluoro-11β-hydroxy-16β-methyl-3-oxo-17α-propionyloxyandrosta-1,4-diene 17β-thiocarboxylate | 0.025 |
| Stearyl Alcohol | 30.0 |
| PEG 6000 | 5.0 |
| 1,2,6-Haxanetriol | 2.5 |
| Citric Acid Anhydrous, USP | 0.02 |
| Propylene Glycol, USP, q.s. | 100.0 |

The steroid is dissolved in 624.8 grams of propylene glycol at 90°–95° C. The latter is then mixed with the other ingredients at 80°–85° C. to give the desired formulation. The subject matter claimed is:

1. A compound chosen from these represented by the formula

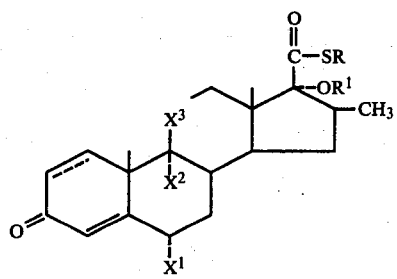

wherein
X¹ is hydrogen or fluoro;
X² is hydrogen, fluoro or chloro;
X³ is

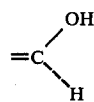

or may also be

when X² is chloro;
R is alkyl of 1 through 6 carbon atoms;
R¹ is alkanoyl of two through six carbon atoms; and
the solid and broken lines between C-1 and C-2 represent a double or single bond.

2. The compound of claim 1 wherein X and X² are both fluoro and R is methyl and R¹ is propionyl, namely methyl 6α,9α-difluoro-11β-hydroxy-16β-methyl-3-oxo-17α-propionyloxy-androsta-1,4-diene 17β-thiocarboxylate.

3. The compound of claim 1 wherein R is methyl, R¹ is propionyl, X¹ is fluoro and X² is hydrogen, namely methyl 6α-fluoro 11β- hydroxy-16 β-methyl-3-oxo-17α-propionyloxy-androsta-1,4-diene 17β-thiocarboxylate.

4. The compound of claim 1 wherein R is methyl, R¹ is propionyl, X¹ is hydrogen and X² is fluoro, namely methyl 9α-fluoro-11β-hydroxy-16β-methyl-3-oxo-17α-propionyloxy-androsta-1,4-diene 17β-thiocarboxylate.

5. A topical anti-inflammatory pharmaceutical composition which comprises a therapeutically effective amount of the compound of claim 1 in combination with at least one suitable pharmaceutical excipient.

6. The compound of claim 1 wherein R is methyl, R¹ is acetyl, X¹ is hydrogen and X² is fluoro, namely methyl 17α-acetoxy-9α-fluoro-11β-hydroxy-16β-methyl-3-oxo-androsta-1,4-diene 17β-thiocarboxylate.

7. The compound of claim 1 wherein R is methyl, R¹ is butyryl, X¹ is hydrogen and X² is fluoro, namely methyl 17α-butyroxy-9α-fluoro-11β-hydroxy-16β-methyl-3-oxo-androsta-1,4-diene 17β-thiocarboxylate.

* * * * *